Figure 1:
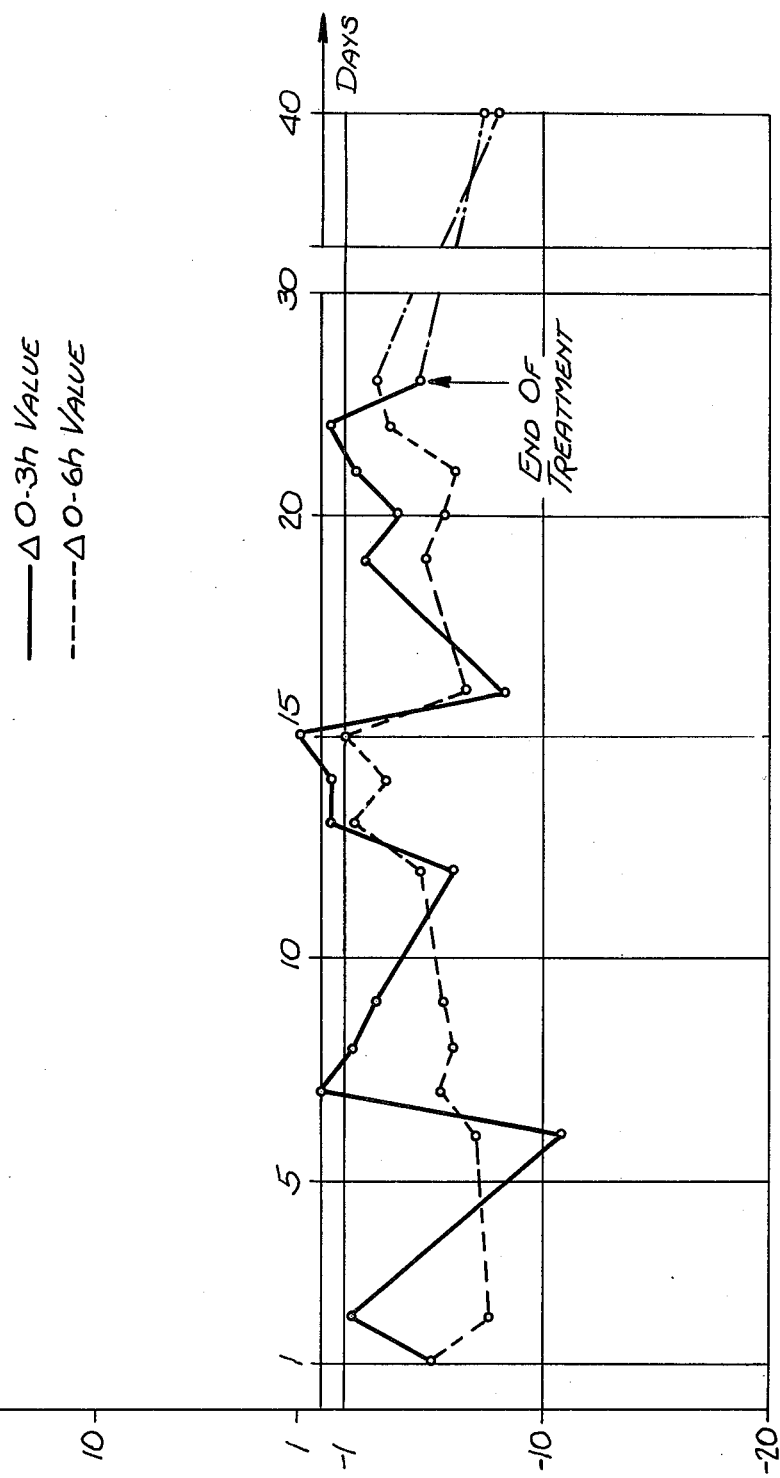

United States Patent [19]
Credner et al.

[11] 3,995,046
[45] Nov. 30, 1976

[54] ESTERS OF 5-n-BUTYLPYRIDINE-2 CARBOXYLIC ACID AND PHARMACEUTICAL COMPOSITIONS CONTAINING THESE COMPOUNDS

[75] Inventors: Karl Credner, Kaarst; Berthold Geisel, Gronau, Leine; Oskar Rohte, Eime ub. Elze; Manfred Tauscher, Gronau, Leine, all of Germany

[73] Assignee: Johann A. Wulfing, Dusseldorf and Neuss, Germany

[22] Filed: Sept. 11, 1975

[21] Appl. No.: 612,453

[30] Foreign Application Priority Data
Sept. 11, 1974 Germany............................ 2443539

[52] U.S. Cl........................... 424/266; 260/294.8 R; 260/295 R

[51] Int. Cl.$^2$............... A61K 31/455; C07D 213/55
[58] Field of Search................ 260/295 R, 294.8 R; 424/266

[56] References Cited
UNITED STATES PATENTS
3,622,587   11/1971   Carlson ........................ 260/295.5R Primary Examiner—Alan L. Rotman
Attorney, Agent, or Firm—Kenyon & Kenyon

[57] ABSTRACT

Novel 3,4,5-trimethoxybenzoyloxyalkyl esters of 5-n-butylpyridine-2-carboxylic acid are superior to the free acid in their ability to reduce mammalian hypertension.

11 Claims, 3 Drawing Figures

ESTERS OF 5-n-BUTYLPYRIDINE-2 CARBOXYLIC ACID AND PHARMACEUTICAL COMPOSITIONS CONTAINING THESE COMPOUNDS 5-n-Butylpyridine-2-carboxylic acid, also referred to as fusaric acid, is known as a metabolite of microorganisms, in particular vegetative germs. 5-n-Butylpyridine-2-carboxylic acid is said to inhibit dopamine-β-hydroxylase, a property which made it appear useful for the treatment of hypertension. However, due to poor lipoid solubility, this promise never was actually realized. Consequently, there is a need for derivatives of 5-n-butylpyridine-2-carboxylic acid which, due to better lipoid solubility, develop a greater biological activity with respect to higher absorption rates.

This invention therefore relates to new esters of 5-n-butylpyridine-2-carboxylic acid of the general formula I:

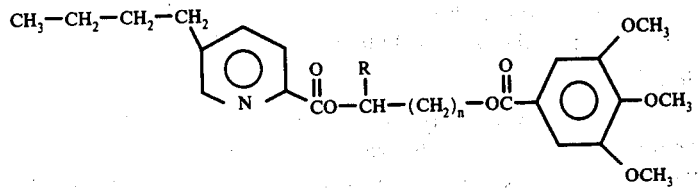

and the pharmaceutically acceptable salts thereof, wherein R is hydrogen or the methyl group and n is 1 to 3. As examples of the new esters, one can mention 1-(5-n-butylpyridyl-2-carboyloxy)-2-(3,4,5-trimethoxybenzoyl)ethane, 2-(5-n-butylpyridyl-2-carboyloxy)-3-(3,4,5-trimethoxybenzoyl)propane, 1-(5-n-butylpyridyl-2-carboyloxy)-3-(3,4,5-trimethoxybenzoyl)propane, 1-(5-n-butylpyridyl-2-carboyloxy)-4-(3,4,5-trimethoxybenzoyl)butane, 2-(5-n-butylpyridyl-2-carboyloxy)-5-(3,4,5-trimethoxybenzoyl)butane, and the like.

The compounds of this invention include not only the free bases as defined by formula (I), but also, as is well known to the art pharmaceutically-acceptable salts of the bases. The chemical nature of such salts, in general, is well known, and includes acid addition salts of inorganic acids, such as the hydrohalic acids, as well as salts of organic acids such as naphthalene-1,5-disulfonic acid. The chemical nature of the acid forming a salt with base (I) is not a feature of this invention, and is not critical provided the salt has the desired anti-hypertensive activity and is pharmaceutically-acceptable, i.e., has no undesirable pharmacologic effects which would preclude use of the salt as an anti-hypertensive agent.

The esters of the present invention can be prepared by either a. reacting a haloalkyl-3,4,5-trimethoxybenzoate with an alkali salt of 5-n-butylpyridine-2-carboxylic acid in polar solvents at elevated temperatures; or b. reacting a hydroxyalkyl-3,4,5-trimethoxybenzoate with 5-n-butylpyridine-2-carboxylic acid chloride in the presence of a condensing agent.

In process (a), the haloalkyltrimethoxy-benzoate starting material has the formula:

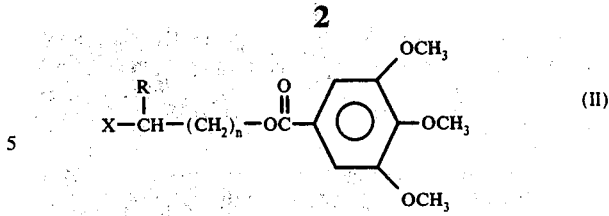

where R and n are as defined above, and X is halogen, e.g. chlorine, bromine or iodine, and preferably is chlorine. The acid salt reacted with (II) can be any alkali metal salt, e.g. a sodium, potassium or lithium salt, with potassium salts being preferred. Polar solvents are well known to the art, and include alcohols such as methoxyethanol, amides such dimethylformamide and dimethylacetamide, and numerous other polar compounds heretofore used as reaction media. Finally, the reaction is effected at elevated temperatures, preferably in the range of from about 80° to about 120° C.

In process (b), the hydroxyalkyl-trimethoxybenzoate starting material has the formula:

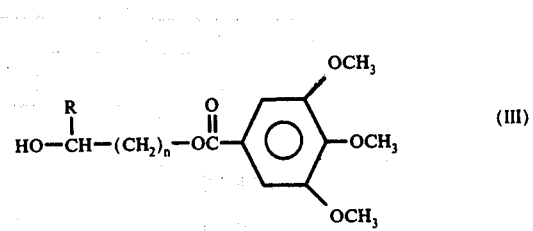

where R and n are as defined above. The process desirably is effected in the presence of a liquid organic base, preferably an aromatic amine such as pyridine and the like, which will serve as a liquid medium for the reaction mixture and as a condensing agent for the reaction, i.e. will combine with the hydrogen chloride released by the reaction. The reaction is readily effected at elevated temperatures.

The new compounds show a distinctly significant activity in the treatment of mammalian hypertension, for example for treating Wistar rats suffering from hypertension induced by throttling the renal artery (Goldblatt method). For such use, the esters of this invention are formed into pharmaceutical compositions which contain at least one compound of the general formula I as an active agent, optionally together with pharmaceutically acceptable carriers and excipients, to provide a unit dosage form of the esters. The esters are administered orally to mammals believed to be suffering from hypertension. The amount of ester administered will vary depending upon the animal, the dosage schedule and the body weight of the mammal being treated. The specific amounts are not a feature of this invention, provided the amount is sufficient to effect a lowering of mammalian blood pressure, and can be easily determined by routine experimentation. In general, however, reduction in mammalian blood pressure has been observed by administering from about 15 to about 50 mg of ester per dose. The dosage may be repeated as necessary.

The following examples serve to illustrate the present invention.

EXAMPLE 1

1-(5-n-Butylpyridyl-2-carbonyloxy)-2-(3,4,5-trimethoxybenzoyloxy) ethane 5.4 g 5-n-Butyl-pyridine-2-carboxylic acid were dissolved in 30 ml 1N-KOH and evaporated to dryness under reduced pressure. The residue was suspended in 200 ml dimethyl formamide and, after addition of 8.24 g 2-chloroethyl-3,4,5-trimethoxybenzoate, heated to 100° with stirring for 3 hours. Upon completion of the reaction, the solvent was distilled under reduced pressure. The residue was taken up in 200 ml benzene and 3 times extracted with portions of 100 ml $Na_2CO_3$ solution. The benzene phase was dried over $Na_2SO_4$ and the solvent removed in a rotation evaporator to give 11.4 g brownish crystals. The product obtained after recrystallization from isopropanol was pure white 1-(5-n-butylpyridyl-2-carbonyloxy)-2-(3,4,5-trimethoxybenzoyloxy)ethane, m.p. 92° C. I.R. (KBr) $v$ : 2833, 1710, 1230 – 1240

Elemental analysis for $C_{22}H_{27}NO_7$ (%):

|  | C | H | N | O |
|---|---|---|---|---|
| required | 63.30 | 6.52 | 3.36 | 26.83 |
| found | 63.20 | 6.48 | 3.30 | 26.90 |

EXAMPLE 2

1-(5-n-Butylpyridyl-2-carbonyloxy)-2-(3,4,5-trimethoxybenzoyloxy)ethane 5.7 g 5-n-Butylpyridine-2-carboxylic acid were refluxed with 20 ml benzene and 20 ml thionyl chloride for 2 hours. The solvent was separated from the reaction product (acid chloride) under reduced pressure. The chloride, after being dissolved in 25 ml pyridine, was added dropwise with stirring for 20 minutes to a mixture of 8.15 g 2-hydroxyethyl-3,4,5-trimethoxybenzoate and 50 ml pyridine. Upon completion of the reaction, the pyridine was distilled off under reduced pressure. The residue was taken up in 100 ml benzene and 3 times extracted with portions of 50 ml sodium carbonate solution. The benzene phase was dried over sodium sulfate and the solvent removed in a rotation evaporator to give 8.4 g of a reddish brown oil which was recrystallized from alcohol to yield 1-(5-n-butyl-pyridyl-2-carbonyloxy)-2-(3,4,5-trimethoxybenzoyloxy)ethane.

EXAMPLE 3

1-(5-n-Butylpyridyl-2-carbonyloxy)-2-(3,4,5-trimethoxybenzoyloxy)ethane 16.0 g 5-n-Butypyridine-2-carboxylic acid were dissolved in 44.6 ml 2N-KOH and evaporated to dryness under reduced pressure. The residue was dissolved in 500 ml methoxyethanol and, after addition of 22.0 g 2-chloroethyl-3,4,5-trimethoxybenzoate, heated to 80° C with stirring for 36 hours. Upon completion of the reaction, the solvent was distilled off under reduced pressure. The residue was taken up in 500 ml benzene and extracted 3 times with portions of 200 ml $Na_2CO_3$ solution. The benzene phase was dried over $Na_2SO_4$ and the solvent removed in a rotation evaporator to give 31.0 g brownish crystals. The product obtained after recrystallization from isopropanol was pure white 1-(5-n-butylpyridyl-2-carbonyloxy)-2-(3,4,5-trimethoxybenzoyloxy) ethane, m.p. 92° C.

EXAMPLE 4

1-(5-*n*-Butylpyridyl-2-carbonyloxy)-3-(3,4,5-trimethoxybenzoyloxy)-propane 10.75 g 5-n-Butylpyridine-2-carboxylic acid, 60.0 ml 1N-KOH and 17.2 g 3-chloropropyl-3,4,5-trimethoxybenzoate were reacted in dimethyl formamide as described in Example 1, and further processed accordingly to yield 23.6 g liquid crude base. Neutralization of the crude base in an alcoholic solution of naphthalene-1,5-disulfonic acid gave 22.4 g of white crystals of 1-(5-n-butylpyridyl-2-carbonyloxy)-3-(3,4,5,-trimethoxybenzoyloxy)propane, m.p. 89° C. I.R. (KBr) $v$ : 1710, 1730, 1115

Elemental analysis for $C_{23}H_{29}NO_7$ (%):

|  | C | H | N | O |
|---|---|---|---|---|
| required | 64.02 | 6.77 | 3.25 | 25.96 |
| found | 64.14 | 6.63 | 3.29 | 25.50 |

EXAMPLE 5

2-(5-n-Butylpyridyl-2-carbonyloxy)-3-(3,4,5-trimethoxy-benzoyloxy) propane 16.0 g 5-n-Butylpyridine-2-carboxylic acid, 90.0 ml 1N-KOH and 21.5 g 2-chloropropyl-3,4,5-trimethoxybenzoate were reacted in dimethyl formamide as described in Example 1, and further processed accordingly to yield 19.7 g liquid crude base. Neutralization of the crude base in an alcoholic solution of naphthalene-1,5-disulfonic acid gave 18.2 g of white crystals, of 2-(5-butylpyridyl-2-carbonyloxy)-3-(3,4,5-trimethoxybenzoyloxy)-propane, m.p. 85° C. I.R. $(CHCl_3)$ $v$ : 1105, 1120, 2830

Elemental analysis for $C_{23}H_{29}No_7$ (%):

|  | C | H | N | O |
|---|---|---|---|---|
| required | 64.02 | 6.77 | 3.25 | 25.96 |

| | C | H | N | O |
|---|---|---|---|---|
| found | 64.09 | 6.69 | 3.29 | 25.50 |

EXAMPLE 6

2-(5-n-Butylpyridyl-2-carbonyloxy)-3-(3,4,5-trimethoxy-benzoyloxy) propane 10.8 g 5-n-Butylpyridine-2-carboxylic acid, 200 ml benzene and 25 ml thionylchloride were refluxed under heating for 2 hours. The solvent was separated from the reaction product under reduced pressure. The acid chloride-hydrochloride taken up in 150 ml benzene was added dropwise with stirring for 20 minutes to a mixture of 14.4 g 3,4,5-trimethoxybenzoate-2-hydroxy-propylester, 250 ml dimethylformamide and 25 ml pyridine. Upon completion of the reaction the solvent mixture was distilled off under reduced pressure. The residue was taken up in 250 ml benzene and extracted 3 times with portions of 100 ml $Na_2CO_3$ solution. The benzene phase was dried over $Na_2SO_4$ and the solvent removed in a rotation evaporator to give 22.0 g of liquid crude base. Neutralization of the crude base with alcoholic naphthalene-1,5-disulfonic acid gave 23.1 g of white crystals the naphthalene-1,5-disulfonic acid salt of 2-(5-n-butylpyridyl-2-carbonyloxy)-3-(3,4,5-trimethoxy-benzoyloxy)propane, m.p. 85° C.

EXAMPLE 7

1-(5-n-Butylpyridyl-2-carbonyloxy)-4-(3,4,5-trimethoxybenzoyloxy) butane 17.9 g 5-n-Butylpyridine-2-carboxylic acid, 100.0 ml 1N-KOH and 28.7 g 4-chlorobutyl-3,4,5-trimethoxybenzoate were reacted in dimethyl formamide as described in Example 1 and further processed accordingly to yield 38.1 g liquid crude base. Neutralization of the crude base in an alcoholic solution of naphthalene-1,5-disulfonic acid gave 30.4 g white crystals of the napthalene-1,5-disulfonic acid salt of 1-(5-n-butylpyridyl-2-carbonyloxy)-4-(3,4,5-trimethoxybenzoyloxy) butane, m.p. 163° C. I.R. ($CHCl_3$) $v$ : 1700, 1715

Elemental analysis for $C_{24}H_{31}NO_7$ (%):

| | C | H | N | O |
|---|---|---|---|---|
| required | 64.70 | 7.01 | 3.14 | 25.13 |
| found | 64.50 | 6.90 | 3.20 | 25.10 |

EXAMPLE 8

Groups of Wistar rats comprising 5 test animals each were administered 1-(5-n-butylpyridyl-2-carbonyloxy)-2-(3,4,5-trimethoxybenzoyloxy)ethane, 5-n-butylpyridine-2-carboxylic acid or NaCl as placebo. The active compounds and placebo were administered in amounts of 30 mg/kg p.o. and 1 ml/kg p.o. (0.9%), respectively. The period of treatment extended over more than 20 days, during which period blood pressures of the test animals were monitored. It was found that animals of the groups which had been given 1-(5-n-butylpyridyl-2-carbonyloxy)-2-(3,4,5-trimethoxybenzoyloxy)ethane had a significantly lower blood pressure on 10 measurements [See Table II, below] than the control group animals, while animals of the group which had been given the reference substance (i.e., 5-n-butylpyridine-2-carboxylic acid) showed a significant reduction in blood pressure only on 6 measurements. [See Table I, below]. When the compounds are compared on the basis of equivalent molar amounts of 5-n-butylpyridine carbonyloxy moiety, it is found that the useful activity of the ester of the present invention is twice as high as that of the reference acid.

Figure 2:
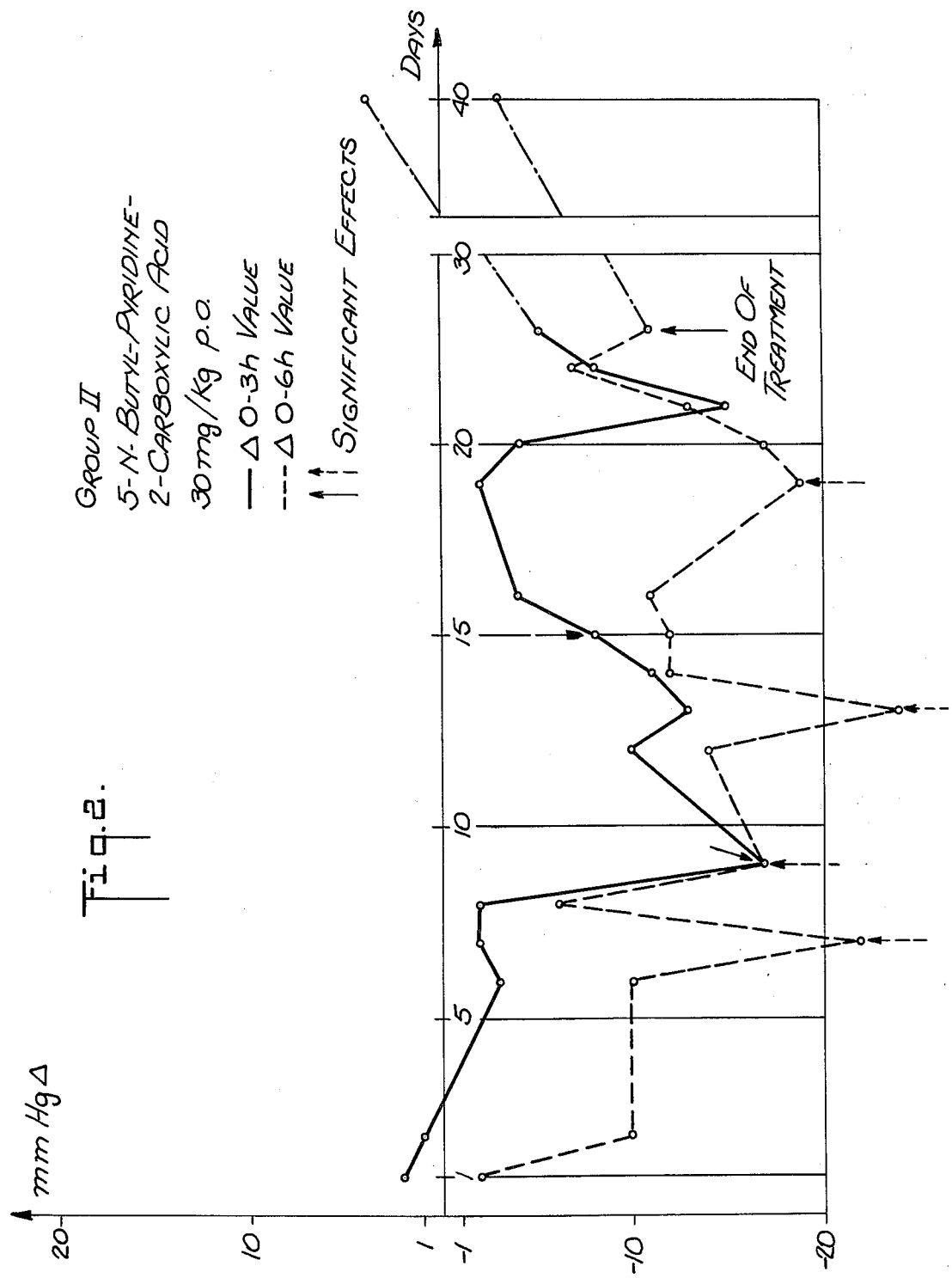
Figure 3:
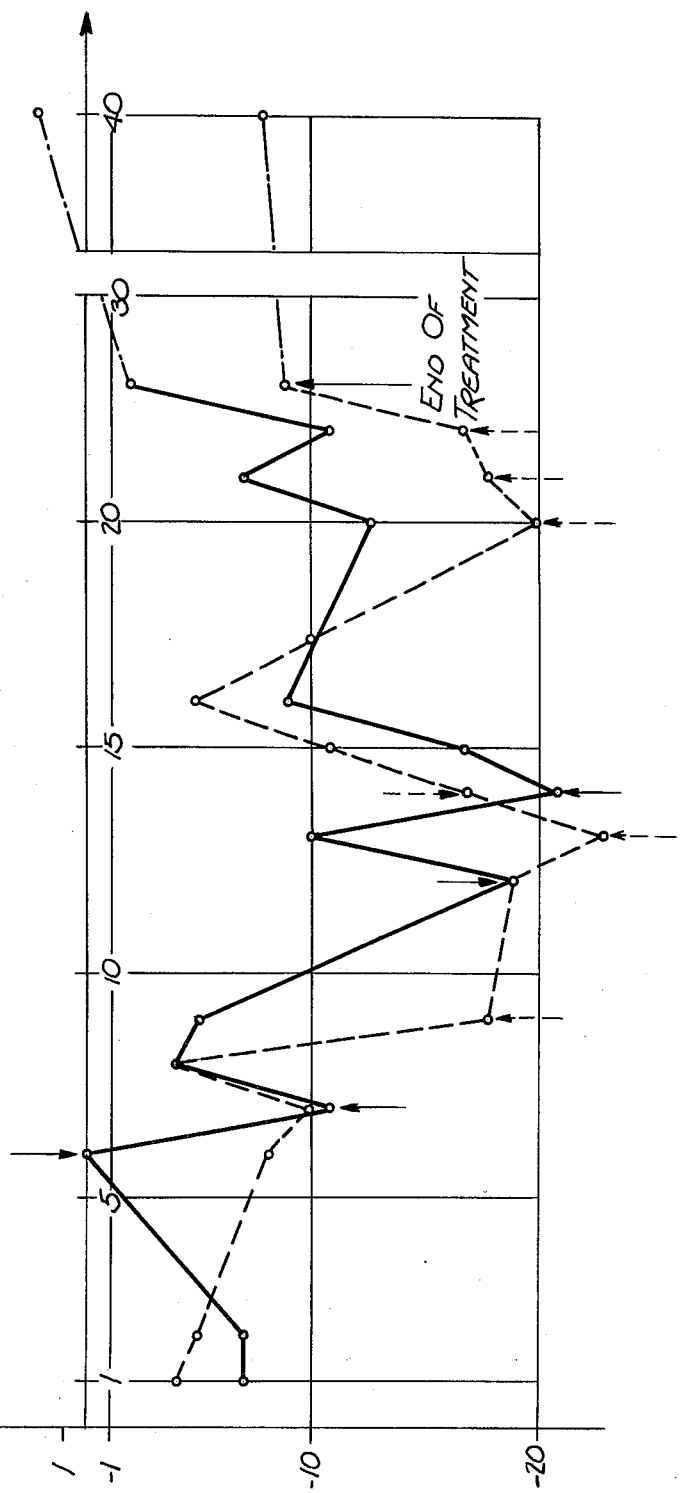

The results of the test series are summarized in the drawings which are graphs of blood pressure measurements against time, wherein FIG. 1 covers the control group, FIG. 2 the reference substance, and FIG. 3 the ester of the present invention.

Table I

Significant Effects of 5-n-Butylpyridine-2-carboxylic acid

| Test day | Student[+] | T-test | Significant after |
|---|---|---|---|
| 1 | T = 2.98 | 0.01 < p < 0.02 | 6 h |
| 3 | T = 2.47 | 0.02 < p < 0.05 | 3 h |
| 3 | T = 2.44 | 0.02 < p < 0.05 | 6 h |
| 7 | T = 3.99 | 0.001< p < 0.002 | 6 h |
| 8 | T = 2.72 | 0.01 < p < 0.02 | 3 h |
| 11 | T = 2.49 | 0.02 < p < 0.05 | 6 h |

Table II

Significant Effects of 1-(5-n-Butylpyridyl-2-carbonyloxy)-2-(3,4,5-trimethoxybenzoyloxy)ethane

| Test day | Student[+] | T-test | Significant after |
|---|---|---|---|
| 1 | T = 2.54 | 0.02 < p < 0.05 | 3 h |
| 2 | T = 2.70 | 0.01 < p < 0.02 | 3 h |
| 4 | T = 2.90 | 0.01 < p < 0.02 | 6 h |
| 7 | T = 2.27 | 0.02 < p < 0.05 | 3 h |
| 8 | T = 3.21 | 0.002< p < 0.01 | 6 h |
| 9 | T = 2.76 | 0.01 < p < 0.02 | 6 h |
| 9 | T = 5.88 | p < 0.0001 | 3 h |
| 15 | T = 2.64 | 0.02 < p < 0.05 | 3 h |
| 15 | T = 3.33 | 0.002< p < 0.01 | 6 h |
| 16 | T = 2.25 | 0.02 < p < 0.05 | 6 h |
| 17 | T = 2.96 | 0.01 < p < 0.02 | 6 h |

[+]See L. Sachs, "Statistische Auswertungsmethoden", Springer-Verlag 1969

We claim:

1. The esters of 5-n-butylpyridine-2-carboxylic acid of the general formula I

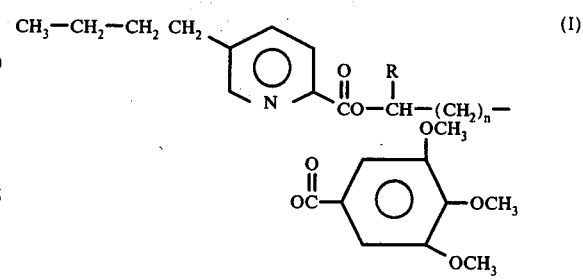

and the pharmaceutically acceptable acid addition salts thereof, wherein R is hydrogen or methyl and $n$ is 1 to 3.

2. An ester according to claim 1 where R is hydrogen.

3. An ester according to claim 2 where $n$ is 1.

4. An ester according to claim 2 where $n$ is 2.
5. An ester according to claim 2 where $n$ is 3.
6. An ester according to claim 1 where R is methyl.
7. An ester according to claim 6 where $n$ is 1.
8. An ester according to claim 6 where $n$ is 2.
9. An ester according to claim 6 where $n$ is 3.

10. A naphthalene-1,5-disulfonic acid salt of an ester according to claim 1.

11. A pharmaceutical composition in unit dosage form containing from 15 to 50 mg of a compound of claim 1 as active agent.

* * * * *